(12) United States Patent
Dantsker et al.

(10) Patent No.: US 10,265,246 B2
(45) Date of Patent: Apr. 23, 2019

(54) SMART BLISTER PACK WITH SKIN PRESENCE TRIGGER

(71) Applicant: CAPSULE TECHNOLOGIES, INC., San Diego, CA (US)

(72) Inventors: Eugene Dantsker, San Diego, CA (US); Robert Ganton, San Diego, CA (US); Robert Ballam, Eatons Hill (AU)

(73) Assignee: CAPSULE TECHNOLOGIES, INC., San Diego, CA (US)

( * ) Notice: Subject to any disclaimer, the term of this patent is extended or adjusted under 35 U.S.C. 154(b) by 0 days.

(21) Appl. No.: 15/673,134

(22) Filed: Aug. 9, 2017

(65) Prior Publication Data

US 2018/0104154 A1   Apr. 19, 2018

Related U.S. Application Data (60) Provisional application No. 62/409,237, filed on Oct. 17, 2016.

(51) Int. Cl.
| | |
|---|---|
| *A61J 7/04* | (2006.01) |
| *A61J 1/03* | (2006.01) |
| *G06F 19/00* | (2018.01) |
| *G08B 29/18* | (2006.01) |

(52) U.S. Cl.
CPC .................. *A61J 7/04* (2013.01); *A61J 1/035* (2013.01); *G06F 19/00* (2013.01); *G06F 19/3462* (2013.01); *A61J 7/0436* (2015.05); *A61J 2200/70* (2013.01); *G06F 19/3456* (2013.01); *G08B 29/181* (2013.01)

(58) Field of Classification Search
CPC .. A61J 1/035; A61J 7/04; A61J 7/0436; A61J 2200/70; G06F 19/3462; G06F 19/00; G06F 19/3456; G08B 29/181
See application file for complete search history.

(56) References Cited

U.S. PATENT DOCUMENTS

| | | | |
|---|---|---|---|
| 5,412,372 | A | 5/1995 | Parkhurst et al. |
| 2003/0007421 | A1 | 1/2003 | Niemiec et al. |
| 2015/0148947 | A1 | 5/2015 | McConville et al. |
| 2015/0274402 | A1 | 10/2015 | Elliott |
| 2015/0283036 | A1 | 10/2015 | Aggarwal et al. |
| 2016/0012710 | A1 | 1/2016 | Lu et al. |
| 2017/0004284 | A1* | 1/2017 | Lesau ............... A61J 1/035 |
| 2017/0294105 | A1* | 10/2017 | Mehregany .......... A61J 1/035 |

FOREIGN PATENT DOCUMENTS

EP     2243460 A1     10/2010

OTHER PUBLICATIONS

International Search Report and Written Opinion—PCT/US2017/052416—ISA/EPO—dated Jan. 2, 2018.

\* cited by examiner

*Primary Examiner* — Ryan W Sherwin (57) ABSTRACT

Techniques provided herein are directed toward accurately determining when an item is removed from a blister pack by utilizing capacitive sensors. The capacitive sensors may be positioned on each blister of the blister and may detect the presence of the skin of the finger and/or the whether the blister has been deformed, which can occur when an item is removed from the blister. Some embodiments may determine whether skin was detected at the time of extraction to determine whether extraction was intentional.

20 Claims, 7 Drawing Sheets

SMART BLISTER PACK WITH SKIN PRESENCE TRIGGER

RELATED APPLICATIONS

This application claims the benefit of U.S. Provisional Application No. 62/409,237, filed Oct. 17, 2016, entitled "SMART BLISTER PACK WITH SKIN PRESENCE TRIGGER", of which is assigned to the assignee hereof, and incorporated herein in its entirety by reference.

BACKGROUND

Oral medication is commonly packaged in "blister packs" whereby each pill (or other item) is housed in a plastic blister with a foil or paper backing that is broken when the pill is "popped out." Being able to detect when a pill is removed from the blister can be valuable to the healthcare provider, insurer, or medication manufacturer because it allows to track medication compliance, adherence, and persistence. But current techniques of determining when a pill is removed can be inaccurate and may not be able to provide any indication of whether a pill may have been removed accidentally.

SUMMARY

Techniques provided herein are directed toward accurately determining when an item is removed from a blister pack by utilizing capacitive sensors. The capacitive sensors may be positioned on each blister of the blister and may detect the presence of the skin of the finger and/or the whether the blister has been deformed, which can occur when an item is removed from the blister. Some embodiments may determine whether skin was detected at the time of extraction to determine whether extraction was intentional.

An example method of determining whether an item has been extracted from a blister pack, according to the description, comprises obtaining data from one or more capacitive sensors of the blister pack, determining, with a processing unit of the blister pack, an item-extraction event occurred based, at least in part, on the data from the one or more capacitive sensors of the blister pack, and sending item-extraction information via wireless communication from the blister pack to an electronic device, the item-extraction information indicative of the item-extraction event.

The method may comprise one or more of the following features. The data from the one or more capacitive sensors of the blister pack can be indicative of an increase in capacitance measured at a blister of the blister pack of at least a threshold amount. The data from the one or more capacitive sensors of the blister pack can be further indicative that the increase in capacitance measured at the blister of the blister pack has been maintained above the threshold for a time period that exceeds a time threshold. The method may further comprise obtaining puncture data indicative of a puncture of backing material of a blister of the blister pack, wherein the determining the item-extraction event occurred is further based on the puncture data. The method may further comprise causing the processing unit of the blister pack to change from a first power state to a second power state based on the puncture data, wherein the processing unit of the blister pack consumes more power in the second power state than in the first power state. The determining the item-extraction event occurred can be further based on obtaining the puncture data and the data from the one or more capacitive sensors of the blister pack within a certain period of time. The puncture data can be obtained from physical breaking of a resistor located in or on the backing material of the blister of the blister pack, or physical breaking of a conductor located in or on the backing material of the blister of the blister pack, or any combination thereof.

According to the description, an example blister pack comprises one or more capacitive sensors, a processing unit communicatively coupled with the one or more capacitive sensors and configured to obtain data from the one or more capacitive sensors and determine an item-extraction event occurred based, at least in part, on the data from the one or more capacitive sensors of the blister pack, and a communication interface configured to wirelessly send item-extraction information from the blister pack to an electronic device, the item-extraction information indicative of the item-extraction event.

The example blister pack may comprise one or more of the following features. The one or more capacitive sensors of the blister pack may be configured to measure an increase in capacitance at a blister of the blister pack of at least a threshold amount. The processing unit may be configured to determine that the increase in capacitance measured at the blister of the blister pack has been maintained above the threshold for a time period that exceeds a time threshold. The blister pack may further comprise puncture-detection sensors configured to obtain puncture data indicative of a puncture of backing material of a blister of the blister pack, wherein the processing unit is configured to determine the item-extraction event occurred further based on the puncture data. The processing unit may be further configured to change from a first power state to a second power state based on the puncture data, wherein the processing unit of the blister pack consumes more power in the second power state than in the first power state. The processing unit may be configured to determine the item-extraction event occurred further based on obtaining the puncture data and the data from the one or more capacitive sensors of the blister pack within a certain period of time. The puncture-detection sensors are configured to obtain the puncture data from physical breaking of a resistor located in or on the backing material of the blister of the blister pack, or physical breaking of a conductor located in or on the backing material of the blister of the blister pack, or any combination thereof.

An example apparatus, according to the description, comprises means for obtaining data from one or more capacitive sensors of a blister pack, means for determining an item-extraction event occurred based, at least in part, on the data from the one or more capacitive sensors of the blister pack, and means for sending item-extraction information via wireless communication from the blister pack to an electronic device, the item-extraction information indicative of the item-extraction event.

The apparatus can comprise one or more of the following features. The means for obtaining data from one or more capacitive sensors of the blister pack may comprise means for obtaining data indicative of an increase in capacitance measured at a blister of the blister pack of at least a threshold amount. The apparatus may further comprise means for determining that the increase in capacitance measured at the blister of the blister pack has been maintained above the threshold for a time period that exceeds a time threshold. The apparatus may further comprise means for obtaining puncture data indicative of a puncture of backing material of a blister of the blister pack, wherein the determining the item-extraction event occurred is further based on the puncture data. The apparatus may further comprise means for causing a processing means of the blister pack to change from a first power state to a second power state based on the puncture data, wherein the processing means of the blister pack consumes more power in the second power state than in the first power state. The means for determining the item-extraction event occurred may comprise means for determining the item-extraction event occurred further based on obtaining the puncture data and the data from the one or more capacitive sensors of the blister pack within a certain period of time. The means for obtaining puncture data comprise means for obtaining puncture data from physical breaking of a resistor located in or on the backing material of the blister of the blister pack, or physical breaking of a conductor located in or on the backing material of the blister of the blister pack, or any combination thereof.

An example non-transitory computer-readable medium, according to the description, has instructions embedded thereon for determining whether an item has been extracted from a blister pack. The instructions include computer code for obtaining data from one or more capacitive sensors of the blister pack, determining an item-extraction event occurred based, at least in part, on the data from the one or more capacitive sensors of the blister pack, and sending item-extraction information via wireless communication from the blister pack to an electronic device, the item-extraction information indicative of the item-extraction event.

The non-transitory computer-readable medium may comprise one or more of the following features. The computer code for obtaining data from one or more capacitive sensors of the blister pack may comprise computer code for obtaining data indicative of an increase in capacitance measured at a blister of the blister pack of at least a threshold amount. The instructions may further comprise computer code for determining that the increase in capacitance measured at the blister of the blister pack has been maintained above the threshold for a time period that exceeds a time threshold. The instructions may further comprise computer code for obtaining puncture data indicative of a puncture of backing material of a blister of the blister pack, wherein the determining the item-extraction event occurred is further based on the puncture data. The instructions may further comprise computer code for causing a processing unit of the blister pack to change from a first power state to a second power state based on the puncture data, wherein the processing unit of the blister pack consumes more power in the second power state than in the first power state. The computer code for determining the item-extraction event occurred comprises means for determining the item-extraction event occurred further based on obtaining the puncture data and the data from the one or more capacitive sensors of the blister pack within a certain period of time. The computer code for obtaining puncture data comprise means for obtaining puncture data from physical breaking of a resistor located in or on the backing material of the blister of the blister pack, or physical breaking of a conductor located in or on the backing material of the blister of the blister pack, or any combination thereof.

BRIEF DESCRIPTION OF DRAWINGS

Non-limiting and non-exhaustive aspects are described with reference to the following figures, wherein like reference numerals refer to like parts throughout the various figures unless otherwise specified.

DETAILED DESCRIPTION

Several illustrative embodiments will now be described with respect to the accompanying drawings, which form a part hereof. The ensuing description provides embodiment(s) only, and is not intended to limit the scope, applicability or configuration of the disclosure. Rather, the ensuing description of the embodiment(s) will provide those skilled in the art with an enabling description for implementing an embodiment. It is understood that various changes may be made in the function and arrangement of elements without departing from the spirit and scope of this disclosure.

Embodiments disclosed herein help determine the removal of an item from a blister pack by utilizing a skin detection circuit whereby the act of pushing out the item with a finger activates a circuit embedded in the blister pack and detects the extraction of an item (otherwise described herein as an item extraction event"). The activation can be accomplished, for example, by virtue of a skin detector that detects a change in the dielectric constant of a capacitive circuit created by the presence of the skin of the finger, which has a different dielectric constant relative to air. Techniques described herein accomplish the task of registering an item extraction event by detecting the proximity of skin to the blister, which occurs during removal of the item in the blister. These techniques can use skin detectors and other components that are workable with existing techniques for manufacturing blister packs.

It can be noted that, although the embodiments described herein are directed toward blister packs, they are not necessarily so limited. As a person of ordinary skill in the art will recognize, techniques herein can be utilized in a variety of applications in which the detection of skin can be used to determine whether a pill or other form of medicine has been dispensed from any type of pill packaging, container, and/or dispenser.

Figure 1:
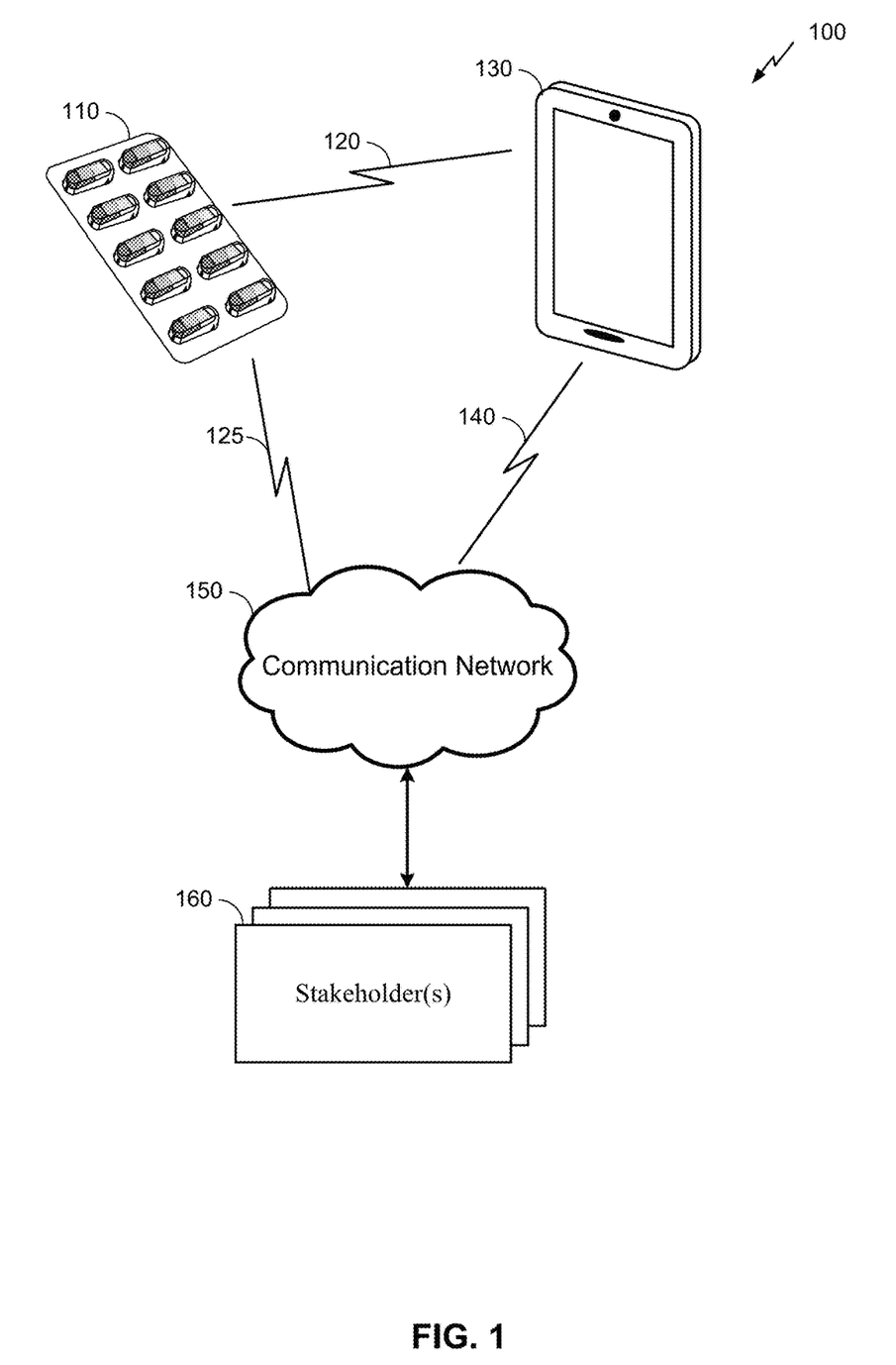
FIG. 1 is an example system for providing information about the administration of medicine by a smart blister pack to one or more stakeholders.

FIG. 1 is an example system 100 for providing information about the administration of medicine by a smart blister pack 110 to one or more stakeholders 160. Here, the system 100 may comprise the smart blister pack 110 as described herein, along with a connecting device 130, communication network 150, and the stakeholder(s) 160. It will be understood, however, that embodiments of a system 100 may include a different configuration of components, the addition and/or omission of various components, and/or the like, depending on desired functionality.

The smart blister pack 110, which is described in more detail herein below, is used to dispense an item such as a drug in the form of a pill (or similarly-formed dosage such as a gelatin capsule ("gelcap"), tablet, etc.) to a patient or other user. The smart blister pack 110 is a type of push-through packaging in which a user usually dispenses the item by using his or her finger to press down on a plastic cavity (or "blister") housing the item, dispensing the item by causing the item to pierce through a foil or paper backing on the smart blister pack 110 with physical force. Once the item is dispensed, the smart blister pack 110 can then register, store, and/or transmit data indicating the item was dispensed to the connecting device 130. This data can be transmitted wirelessly via a wireless communication link 120 (which may be encrypted) using any of a variety of wireless technologies, as described in further detail below.

It can be further noted that although embodiments described herein are directed toward detecting the skin of a user, other embodiments are not so limited. Embodiments can include detecting features of and/or related to a user (in addition to or instead of the skin) that can be detected using the detection means described herein, or similar features.

The connecting device 130 may comprise any of a variety of electronic devices capable of receiving information from the smart blister pack 110 and communicating information to the stakeholder(s) 160 via the communication network 150. This can include, for example, a mobile phone, tablet, laptop, portable media player, personal computer, or similar device. In some embodiments, the connecting device 130 may comprise a specialized device utilized for purposes of conveying information from the smart blister pack (and possibly other drug dispensers and/or medical devices) to the stakeholder(s) 160.

The connecting device 130 may execute an application to provide the data processing and/or relaying functionality illustrated in FIG. 1. In some embodiments, the application may be configurable by a user, or may simply be downloaded to the connecting device 130 and executed automatically with little or no user input. The application may help establish the communication link 120 between the smart blister pack 110 and the connecting device 130, which may or may not require input from the user, depending on desired functionality. In some embodiments, the application may provide instructions to a user on proper use of the smart blister pack 110 and/or feedback to a user when improper use of the smart blister pack 110 is detected (e.g., where detection circuitry detects that an item has been dispensed without the detection of skin, which could be an indication that the item was dispensed accidentally). In some embodiments, such where the item is a pill (or other form of drug), the connecting device 130 may further be used to confirm (e.g., via a user interface) that a patient has dispensed and/or taken a pill. For example, the detection of a pill being dispensed may evoke the user interface, which the patient may then use to indicate whether the extraction was intentional and/or whether the drug was taken. User confirmation may further include confirmation that the pill was taken correctly (e.g., swallowed, with water, food, etc.). Additional and/or alternative functionality of an application executed by the connecting device 130 may be utilized as desired. (As noted elsewhere herein, such functionality includes simple relaying of the data to a remote destination or interacting with the patient about the drug administration such as confirmation and user feedback.)

The communication network 150 may comprise any of a variety of data communication networks, depending on desired functionality. The communication network 150 can include any combination of radio frequency (RF), optical fiber, satellite, and/or other wireless and/or wired communication technologies. In some embodiments, the communication network 150 can comprise the Internet and/or different data networks (including public and/or private data communication networks). The communication link 120, the communication link 140, and/or the communication network 150 may utilize any of a variety of technologies, including cellular, Wi-Fi®, and/or other wireless technology. These technologies may include, for example, Code Division Multiple Access (CDMA) communication, Time Division Multiple Access (TDMA) communication, Frequency Division Multiple Access (FDMA) communication, Orthogonal Frequency Division Multiple Access (OFDMA) communication, Single-Carrier Frequency Division Multiple Access (SC-FDMA) communication, WiMax (IEEE 802.16), and so on. CDMA communication may implement one or more radio access technologies (RATs) such as cdma2000, Wideband-CDMA (W-CDMA), and so on. Cdma2000 includes IS-95, IS-2000, and/or IS-856 standards. TDMA communication may implement Global System for Mobile Communications (GSM), Digital Advanced Mobile Phone System (D-AMPS), or some other RAT. OFDMA communication may employ LTE (including CATM, or 5G), LTE Advanced, and so on. LTE, LTE Advanced, GSM, and W-CDMA are described in documents from 3GPP. Cdma2000 is described in documents from a consortium named "3rd Generation Partnership Project 2" (3GPP2). 3GPP and 3GPP2 documents are publicly available. The communication link 120, the communication link 140, and/or the communication network 150 may additionally or alternatively include or be a part of a wireless local area network (WLAN), ZigBee® network, and/or a wireless personal area network (WPAN). Additionally or alternatively, the communication link 120, the communication link 140, and/or the communication network 150 utilize Bluetooth (including Bluetooth Low Energy), IEEE 802.15x, IEEE 802.11x, and/or another RF communication technology. The techniques described herein may also be used for any combination of wireless wide area network (WWAN), WLAN and/or WPAN. In embodiments where the connecting device 130 is a personal computer, the communication link 140 may comprise a wired communication link that accesses the medication network 150 via a cable or digital subscriber line (DSL) modem.

It can be noted that some embodiments may not utilize a connecting device 130 to relay data to the communication network 150. In such embodiments, the smart blister pack 110 (or similar device) may connect directly to the communication network 150 (as shown in FIG. 1 by communication link 125 which may be used in addition or as an alternative to communication link 120). For example, the smart blister pack 110 may comprise a Long Term Evolution (LTE) category M (CatM) device. Additionally or alternatively, the smart blister pack 110 may wireless functionality similar to the corresponding functionality of the connecting device 130 described above. In such embodiments, the communication network may additionally or alternatively comprise a Bluetooth Mesh network (such as CSRMesh), a WiFi network, Zigbee, or WWAN (such as LTE, including CATM, or 5G).

As noted above, the stakeholder(s) 160 may include any of a variety of entities with an interest in a pill being dispensed from the smart blister pack 110. This can include an individual practitioner (e.g., a doctor or nurse), a hospital, a drug manufacturer, an insurance provider (or other payer), a government agency or other health organization, and/or the like. In some embodiments, the user of the smart blister pack 110 (e.g., the patient) may also be a stakeholder 160 to which information regarding the use of the smart blister pack is provided. Governmental health regulations and/or legal agreements between the patient and/or the stakeholder(s) 160 may apply to the dissemination of information regarding the dispensation of medicine by the smart blister pack 110 to the stakeholder(s) 160. Here, the smart blister pack 110 can utilize a skin presence sensor to help ensure the accuracy of the information disseminated to the stakeholder(s) 160.

Figure 2A:
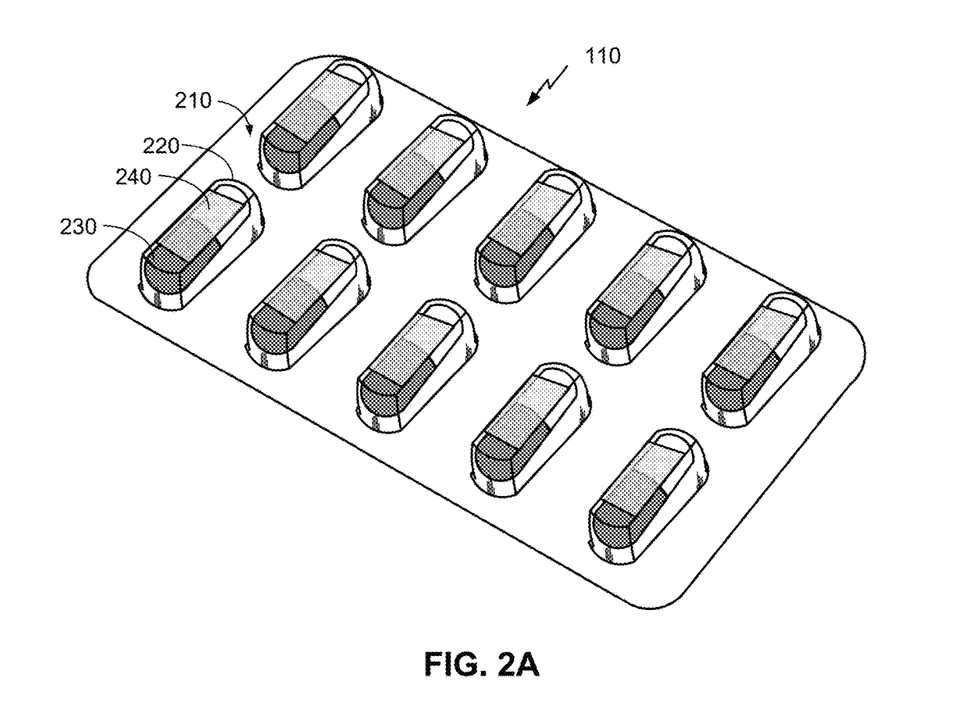
FIGS. 2A and 2B are simplified perspective views of the top and bottom sides of a smart blister pack, respectively, according to embodiments herein.
Figure 2B:
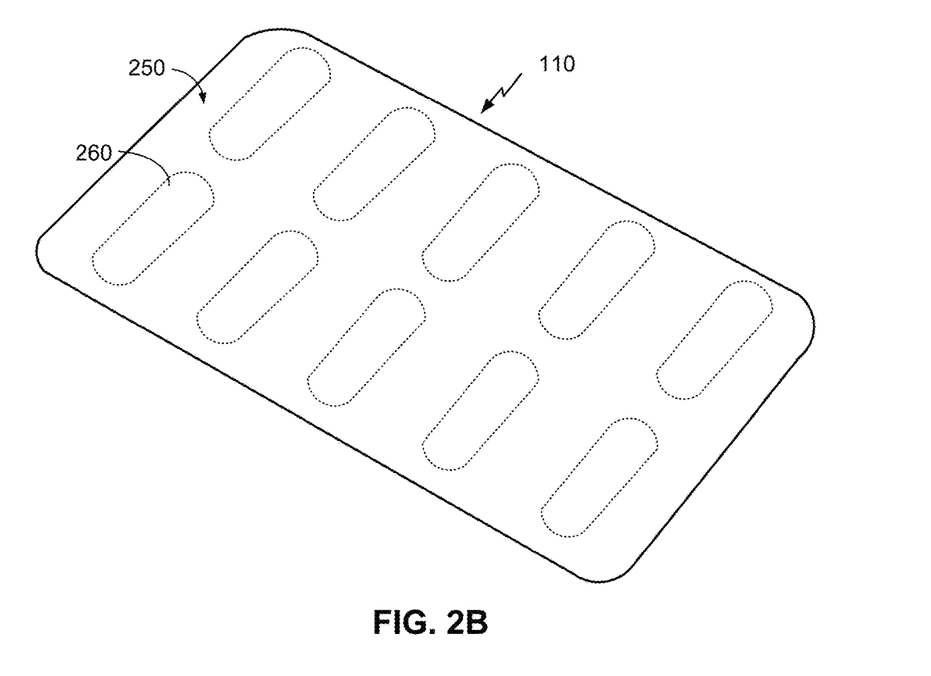

FIGS. 2A and 2B are simplified perspective views of the top and bottom sides of a smart blister pack 110, respectively, according to embodiments herein. It can be noted, however, that smart blister packs can generally come in many shapes, sizes, and forms, and may dispense items the various ways. As with traditional blister packs, a smart blister pack 110 is generally intended to be disposed once all items packaged therein have been dispensed. That said, the techniques described herein may be utilized with non-disposable packaging or container in which the detection of skin can be used to determine whether an item has been dispensed.

The top side of the smart blister pack 110, illustrated in FIG. 2A, is similar to traditional blister packs in that embodiments may have a top layer 210 comprising a layer of plastic, although other materials may be used. This layer can comprise one or more cavities (or "blisters") 220, each of which houses an 230, such as a pill, tablet, etc. The smart blister pack 110 can be used in a manner similar to traditional blister packs to dispense items 230. That is, a patient (or other user) can press down on a cavity 220, causing the cavity to deform (e.g., the roof of the cavity to press down on the item) such that the item pierces through backing material on the bottom of the smart blister pack 110. In some embodiments, the smart blister pack may include an additional cavity or other compartment (not shown) to house the electrical circuitry and/or power source (e.g., battery).

FIG. 2B illustrates the bottom of the smart blister pack 110, having a bottom layer 250 comprising a layer of foil, paper, or other backing material. The bottom also includes one or more portions 260 (which are on the bottom of the cavities 220) through which items will be dispensed (e.g., by piercing the foil, paper, etc. of layer 250). That said, in some instances an item may be dispensed by piercing through the top layer 210 of the smart blister pack 110 (e.g., through the wall or roof of a cavity 220).

Referring again to FIG. 2A, the smart blister pack 110 further comprises skin detectors 240 situated on the cavities 220 (and/or otherwise disposed on the smart blister pack 110) to detect when an item is dispensed by the smart blister pack 110. That is, skin detectors 240 can be located on the portion (e.g., at or near the top) of cavities 220 that is pushed by the user to extract the item. When the skin of the user's finger is detected by the skin detector 240, the smart blister pack 110 can make a determination of whether an item has been extracted (e.g., whether an item extraction event has occurred). This determination can be made based on input from the skin detector 240. This may not only include an indication from the skin detector 240 that skin was detected, but also an indication of a duration of time during which the skin detector 240 detected skin, as well as other factors.

A skin detector 240 may utilize any of a variety of technologies for skin detection. In some embodiments, for example, a skin detector 240 may comprise a capacitive element, capable of determining a change in capacitance or dielectric constant when in contact or near a user's skin. Accordingly, in such embodiments, when a patient uses his or her finger to press down on a cavity 220 to dislodge the item 230 disposed therein, the skin detector 240 will experience a relatively large change in capacitance. This change in capacitance can be measured by measurement circuitry (not shown) to determine the presence of a user's skin.

Some embodiments may further measure capacitance after the initial detection of a user's skin to further inform a determination of whether an item has been extracted. For example, in embodiments in which a skin detector 240 measures capacitance and the bottom layer 250 has a measurable capacitance (e.g., comprises foil), the measured capacitance by the skin detector 240 may be different after the cavity 220 is deformed because the skin detector 240 may be nearer to the bottom layer 250. Accordingly, when the capacitance measured before the detection of skin is determined to be lower than the capacitance measured after the detection of skin, then the smart blister pack 110 may determine that an item extraction event occurred because this difference in measured capacitance is indicative of the deformation of the cavity 220, which typically only happens when an item is extracted. In some embodiments, a smart blister pack 110 may only determine that an item extraction event occurred when this difference in capacitance is larger than a predetermined threshold.

An example of a skin detector 240 that could be utilized in a smart blister pack 110 is described in further detail in U.S. Pat. No. 9,459,089, entitled "METHOD, DEVICES AND SYSTEMS FOR DETECTING AN ATTACHMENT OF AN ELECTRONIC PATCH" filed Aug. 14, 2014, which is assigned to the assignee hereof and Incorporated by reference herein for all purposes.

A smart blister pack 110 may utilize skin detectors 240 as illustrated in FIG. 2A in addition or as an alternative to other technologies that help determine an item extraction event. One such technology is illustrated in FIG. 3.

Figure 3:
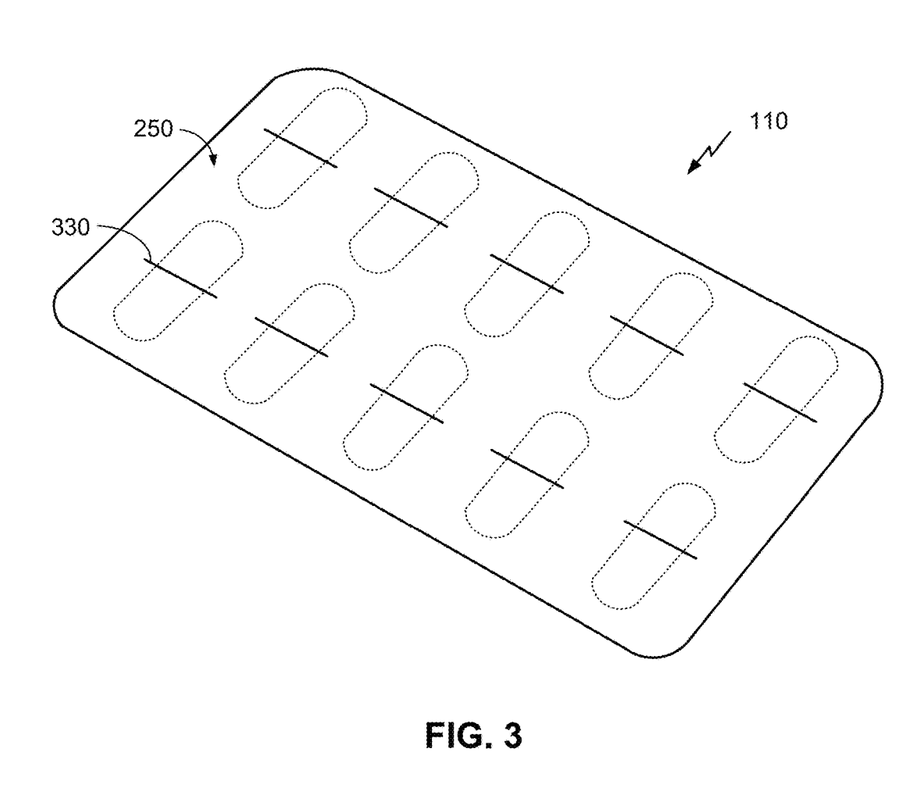
FIG. 3 is an illustration of the bottom side of a smart blister pack according to another embodiment.

FIG. 3 is an illustration of the bottom side of a smart blister pack 110 according to another embodiment. Here, the smart blister pack 110 includes a puncture-detection element 330 situated on the bottom of each blister such that, when an item is extracted from a blister of the smart blister pack 110 the puncture-detection element 330 is broken. Circuitry connected to the puncture-detection element 330 can detect a change in the conductivity or resistivity of the puncture-detection element 330, which can indicate an item extraction event. For example, in some embodiments the detection element may comprise an element with a known conductivity or resistivity that connects an output of a microprocessor to a voltage (e.g., a power supply voltage or ground). When the detection element is broken, the microprocessor can detect the change in voltage on the output and, based on that detection, determine whether an item extraction event occurred. In alternative embodiments, other types of circuitry may be utilized in a similar manner to detect a change in conductivity of the puncture-detection element 330. In some embodiments, the puncture-detection element 330 may have a relatively high resistance (e.g., on the order of mega ohms or higher) to help ensure low current draw. This can be used in addition or alternative to the use of skin detectors 240 to help accurately determine an item extraction event. Similar to the skin detectors 240, each puncture-detection element may correspond with a particular blister such that the smart blister pack 110 can determine an item extraction event for each individual blister in the smart blister pack 110. It will be appreciated by a person of ordinary skill in the art that puncture-detection elements 330 may take any of a variety of shapes or patterns and may be disposed on the smart blister pack 110 in a variety of ways to detect when the bottom layer 250 of the smart blister pack 110 has been punctured by an item.

Features of the puncture-detection element 330 can vary, depending on desired functionality. According to some embodiments, for example, the puncture-detection element 330 may be a trace of conductive material (e.g., a material having a known conductivity or resistivity) disposed on the bottom layer 250 of the smart blister pack 110 or in/on some intermediary layer (e.g., between the top layer 210 (of FIG. 2A) and a bottom layer 250). In embodiments where the bottom layer 250 is conductive, there may be a layer of insulating material between the bottom layer 250 and the puncture-detection element 330. In some embodiments, the puncture-detection element 330 may comprise a trace of carbon, which may be easy to implement using current blister pack manufacturing techniques because traces of carbon can be implemented with an additive film on the bottom layer 250 of the smart blister pack 110.

It can be noted that embodiments may use other types of elements in a similar manner. That is, rather than using one or more puncture-detection elements 330, embodiments may similarly use capacitive and/or inductive elements in a similar manner, where the elements have a capacitance and/or inductiveness that changes when the bottom layer 250 is pierced and the element is broken. And circuitry measuring the capacitance and/or inductiveness may detect this change and determine whether an item extraction event occurred in a manner similar to the detection elements described above. The material comprising the bottom layer 250 may impact what type of puncture-detection elements 330 may be used.

Alternatively, some embodiments may not utilize puncture-detection elements 330 where other circuitry can detect an item extraction event with sufficient accuracy. For example, as previously mentioned, a capacitance-based skin detector 240 may detect permanent deformation in the plastic (or other material) forming the cavity 220. In these embodiments, an item extraction event may be detected when the skin detector 240 detects the presence of skin followed by a deformation of the plastic cavity 220. In such instances, puncture-detection elements 330 may not be needed to accurately determine an item extraction event. Even so, other embodiments may employ both skin detectors and puncture detection elements 330 to increase the accuracy of the detection of an item extraction event even further.

As previously mentioned, puncture-detection elements 330 as shown in FIG. 3 can be used by a smart blister pack 110 to complement the use of skin detectors 240 and more accurately determine an item extraction event and whether the item extraction event was intentional. For instance, a skin detector 240 may detect the presence of a user's skin when the user is handling the smart blister pack 110, without extracting any items. In such instances, if the smart blister pack detects the presence of a user skin but does not detect any change in the conductivity of a puncture-detection element 330, then the smart blister pack may determine that no item extraction event occurred. In other instances, the smart blister pack 110 may be subject to unintentional forces (e.g., squeezed between items in a person's bag), causing an item to be extracted unintentionally. In that case, the smart blister pack 110 may detect the change in conductivity of a puncture-detection element 330, but a skin detector 240 may not detect the presence of any skin (e.g., in the corresponding cavity 220 at substantially the same time as the change in conductivity of the puncture-detection element 330), and/or may not detect the presence of skin for a threshold amount of time. As such, the smart blister pack 110 may determine that an item was extracted, and that the item was extracted unintentionally. In such instances, the smart blister pack 110 may send a message to the user's cell phone (e.g., connection device 130 of FIG. 1), causing the user cell phone to convey an audio and/or video message to the user that an unintended item extraction event occurred.

It can be noted that embodiments of the smart blister pack 110 as described herein can be useful for more than just item extraction detection. As noted elsewhere herein, information may be stored on a processor of the smart blister pack 110 and convey to user (e.g., via an app, executed by the user's cell phone, and configured to show information on the cell phone's display). This information can include instructions, warnings, expiration information, and/or other information regarding the items.

The smart blister pack 110 may further provide for interactivity based on user input. For example, in a mixed blister pack including a plurality of item types (e.g., different pill types), a blister pack may be able to detect a blister touched by user and identify (via the user cell phone, for example) the type of pill contained in the touched blister, information regarding when/how the pill contained in the touched blister should be taken, etc. That is, just as a pill extraction event may be transmitted from a smart blister pack 110 to a user's cell phone, a touch event may be similarly communicated to the user's cell phone (indicating, for example, which blister is/was touched), enabling an application on the user's cell phone to display corresponding information regarding the pill within the touched blister.

Other such interactivity based on the touching of a blister m or alternatively may additionally be implemented. For instance, in some embodiments, a touch event may trigger a warning if a pill within a touched blister should not be taken. That is, if a user's mobile phone receives a touch event from the smart blister pack 110 and determines that a pill contained within the touched blister should not yet be taken, the mobile phone can display a warning to the user and/or provide another alert that it is not yet time to take the pill. Additionally or alternatively, a touch event (and/or corresponding alert) may be communicated to a healthcare provider, caregiver, and/or other stakeholder 160. Embodiments of a smart blister pack 110 may further be configured to guard against false positives, by determining when (despite certain sensor input) an item extraction event has not taken place. In some embodiments, input from different sensor types may be weighted differently in a determination of whether an item extraction event occurred and/or how it occurred. For example, the skin detector of a particular blister on the smart blister pack 110 may detect contact and/or blister deformation, but if a corresponding puncture-detection element for the blister does not indicate a puncture, the smart blister pack may determine that the item in the blister was not dislodged. Similarly, if a puncture-detection element for a blister indicates that the item was dislodged (that a puncture took place) without the skin detector detecting the presence of skin at substantially the time of dislodgement (e.g., within a certain time threshold), then it may be determined that the item was dislodged accidentally. Additionally, the smart blister pack 110 can track which blisters have been opened so that subsequent sensor data from skin sensors and/or puncture-detection elements for those blisters are not considered additional item extraction events.

A smart blister pack 110 may additionally or alternatively use one or more detection elements 330 for purposes of power management. That is, puncture-detection elements 330 can be used to quickly cause a microprocessor to transition out of a low-power state. For example, some embodiments of a smart blister pack 110 may utilize skin detectors 240 that require periodic capacitive sampling to detect the presence of skin. This may cause the microprocessor executing the capacitive sampling to operate at a state that requires some current draw (e.g., the microprocessor may be operating a low-frequency clock requiring a current draw in the μA range). Thus, to save power, embodiments may use puncture-detection elements 330 which, because they do not require periodic sampling in the same manner as the skin detectors 240, they can allow the microprocessor to operate in a low-power state (e.g., a "halted" or very low-frequency state, where current draw is in the nA range) one of the puncture-detection elements 330 is broken. At that point, the microprocessor can quickly execute capacitive sampling, causing the skin detectors 240 to detect whether skin is present and/or whether a capacitive change has occurred in a cavity 220 of the smart blister pack 110.

In some embodiments, a triggering event (e.g., an indication that a puncture-detection elements 330 is broken) may cause a microprocessor of the smart blister pack 110 may awake from a very low-power or halted state to operate in a state in which capacitive sampling takes place. For embodiments in which all items of the smart blister pack 110 are typically extracted within days or weeks from the extraction of the first item (e.g., for embodiments in which the items are pills or tablets), then this type of sampling may be acceptable because extending battery life may not be as important.

In some embodiments, a smart blister pack 110 may have a "shelf mode" and an "active mode" in which the microprocessor samples skin detectors 240 at different rates for power management. In such embodiments, the microprocessor may sample skin detectors 240 at a relatively slow rate (e.g., at a rate of once every 1 second, 2 seconds, 5 seconds, or the like) until a triggering event is detected. Here, a triggering event may comprise an item extraction event (e.g., the detection of a change of capacitance above a threshold level), an activation event (e.g., the smart blister pack is activated by a pharmacist or other entity by pressing a button, opening a package, etc., which may be detected by sensors and/or other input), or other event that causes the microprocessor to enter an active mode. In the active mode, the microprocessor may sample skin detectors 240 at a relatively faster rate (e.g., at a rate of once every 100 ms or so), to help ensure accuracy in the detection of an item extraction event. In this way, some embodiments may detect and optionally report an item extraction event in real time. A person of ordinary skill in the art will appreciate that various considerations may be taken into account to balance shelf life/power consumption with accuracy in the detection of item extraction.

Figure 4:
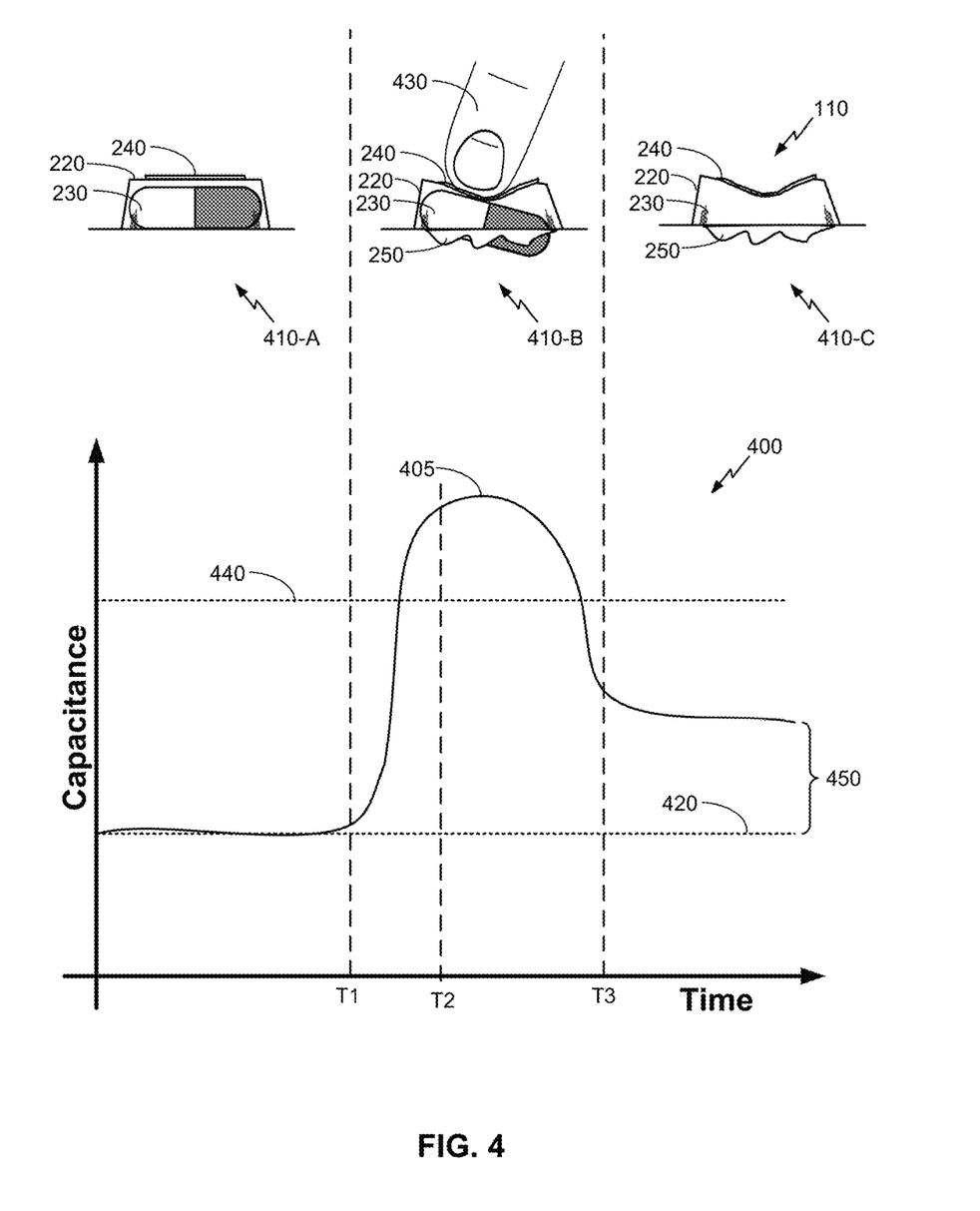
FIG. 4 is an illustration of how an item extraction event may be determined by a smart blister pack, according to an embodiment.

FIG. 4 is an illustration of how an item extraction event may be determined by a smart blister pack, according to an embodiment. FIG. 4 includes a graph 400 of measured capacitance 405 from a skin detector 240 of a cavity 220 (or blister) of the smart blister pack, as well as illustrations 410-A, 410-B, and 410-C (collectively referred to as 410) illustrating a cross-section of the cavity 220 of the smart blister pack during certain periods of time corresponding to the graph 400. Here, the graph 400 is provided for illustrative purposes only. A person of ordinary skill in the art will appreciate that actual measured capacitance 405 may vary from that which is shown in FIG. 4, depending on various factors.

As indicated above, a skin detector 240 can measure the presence of a finger and/or the deformation of the cavity 220 by measuring increases in capacitance. Before time T1 (see illustration 410-A) (prior to the extraction of the item 230 from the cavity 220), the initial measured capacitance 420 is relatively low.

After time T1, however, a user's finger 430 presses against the skin detector 240, deforming the cavity 220 and causing the item 230 to break through the bottom layer 250 of the smart blister pack (see illustration 410-B). Because of the presence of the finger 430 and the deformation of the cavity 220, there is a substantial increase in measured capacitance 405. Some embodiments may have a threshold 440 that a processing unit (receiving capacitance measurements from the skin detector 240) can use to determine whether a finger is detected by the skin detector 240. In FIG. 4, because measured capacitance 405 increases over the threshold 440, the processing unit may determine that a user's finger 430 is present between times T1 and T3.

As indicated above, embodiments may utilize additional information to determine an item extraction event and/or whether the item extraction event was intentional. For example, the processing unit may receive an indication at time T2 from a puncture-detection element corresponding to the cavity 220 that the bottom layer 250 of the cavity 220 has been punctured. Because this puncture-detection data is received at substantially the same time that the finger 430 is detected (capacitance is above the threshold 440) and/or within a window of time (e.g., between times T1 and T3) during which the finger 430 is detected, the processing unit may determine that an item extraction event has occurred, and that the item was extracted intentionally.

After time T3, when the user's finger 430 has been removed from the skin detector 240 and the item 230 has been extracted from the cavity 220, the measured capacitance may still be higher than the initial measured capacitance 420. As explained previously, this is because the deformation of the cavity 220 can cause the skin detector 240 to be closer to the bottom layer 250 of the smart blister pack which (in this example at least) has a measurable capacitance (see illustration 410-C). In some embodiments, the processing unit can determine whether the difference in measured capacitance 450 is greater than a certain threshold to determine whether the formation of the cavity 220 has occurred. The processing unit can then use that information (indicating whether the cavity 220 has been deformed or not) as an additional data point in determining whether an item extraction event has taken place at that cavity 220.

Alternative embodiments may measure item extraction in different ways, depending on desired functionality. As previously mentioned, some embodiments may not measure capacitance at a given cavity 220 until puncture-detection data has been received for that cavity 220. For example, when puncture-detection data is received for a given cavity 220, the smart blister pack can then actively sample the skin detector 240 for the cavity 220 (and optionally other cavities of the smart blister pack) every 100 ms for a certain period of time (e.g., 1-5 seconds) after the puncture-detection data has been received, in order to accurately detect the presence of a user's finger 430. In other embodiments, puncture-detection data from any cavity 220 of the smart blister pack may cause the smart blister pack to exit a "shelf mode" and regularly measure capacitance thereafter (e.g., periodically every 1-5 seconds) until all items have been extracted from the smart blister pack. That said, in some embodiments, the smart blister pack may be configured to re-enter a shelf mode if a threshold amount of time (e.g., a "shelf mode" threshold) passes without any further indication of use (e.g., skin-detection and/or puncture-detection events) of the smart blister pack.

In some embodiments, such as those measuring capacitance at a relatively infrequent rate (e.g., to save on battery life) and therefore may not detect the presence of a user's finger 430 in real time, the processing unit can detect an item extraction event based on the difference in measured capacitance 450 of a cavity 220 between a first time and a second time is greater than a certain threshold, and/or that puncture data for that cavity 220 indicates extraction has occurred.

Figure 5A:
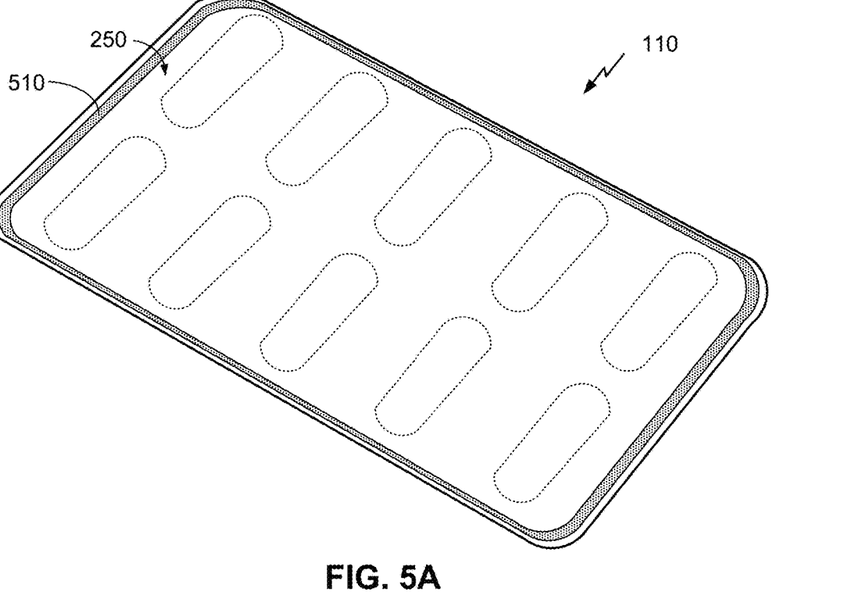
FIGS. 5A and 5B are illustrations of the bottom side of a smart blister pack according to other embodiments.
Figure 5B:
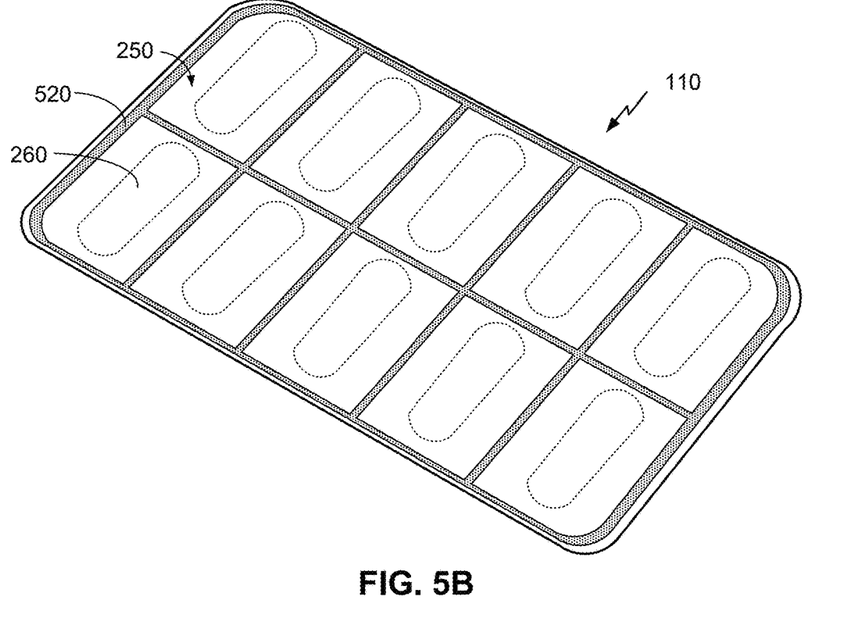

In yet another embodiment, the user's finger 430 may be contacting the edge of the blister pack in preparation to perform a pill extraction. A capacitance sensor can be positioned around the natural holding area of the blister pack to detect when a user is about to release an item. This measurement could be done directly after an item extraction to validate that a user has been and is still handling the packaging and is intentionally removing an item. FIGS. 5A and 5B illustrate embodiments of how a capacitance sensor may be positioned around the natural holding area of the blister pack.

FIGS. 5A and 5B are illustrations of the bottom of a smart blister pack 110, according to different embodiments. It can be noted that, embodiments may also include puncture detection elements 330, as illustrated in FIG. 3. The material of the bottom layer 250 may need to be selected to be compatible with the illustrated capacitive sensors. As noted above, a capacitive sensor can be positioned to detect when a user is about to release an item. For example, a single capacitive sensor 510 in FIG. 5A is located around the periphery of the bottom of the smart blister pack 110.

In FIG. 5B, portions of a capacitive sensor 520 run between portions 260 forming the bottom of the cavities 220 (see FIG. 2A) of the smart blister pack 110 to detect the presence of a finger (or other capacitive object) in these areas. The idea here is that a person naturally places their fingers on the rigid area between the blisters and/or the edge of the smart blister pack 110 in order to dislodge an item (e.g., pill) from a blister.

With regard to both FIGS. 5A and 5B placing the capacitive sensor 510, 520 as illustrated would entail applying films on a flat surface (bottom layer 250). With embodiments having puncture-detection elements 330 (see FIG. 3) the capacitive sensor 510, 520 could be applied on the same film as the puncture-detection elements 330 so it would not add any additional steps in the manufacturing process. This can be relatively easy to do in production and it should provide enough additional information to confirm an intentional pill extraction event.

It will be understood that, although each figure includes a single capacitive sensor 510, 520, multiple capacitive sensors could be arranged to cover a similar portion of the smart blister pack 110.

Figure 6:
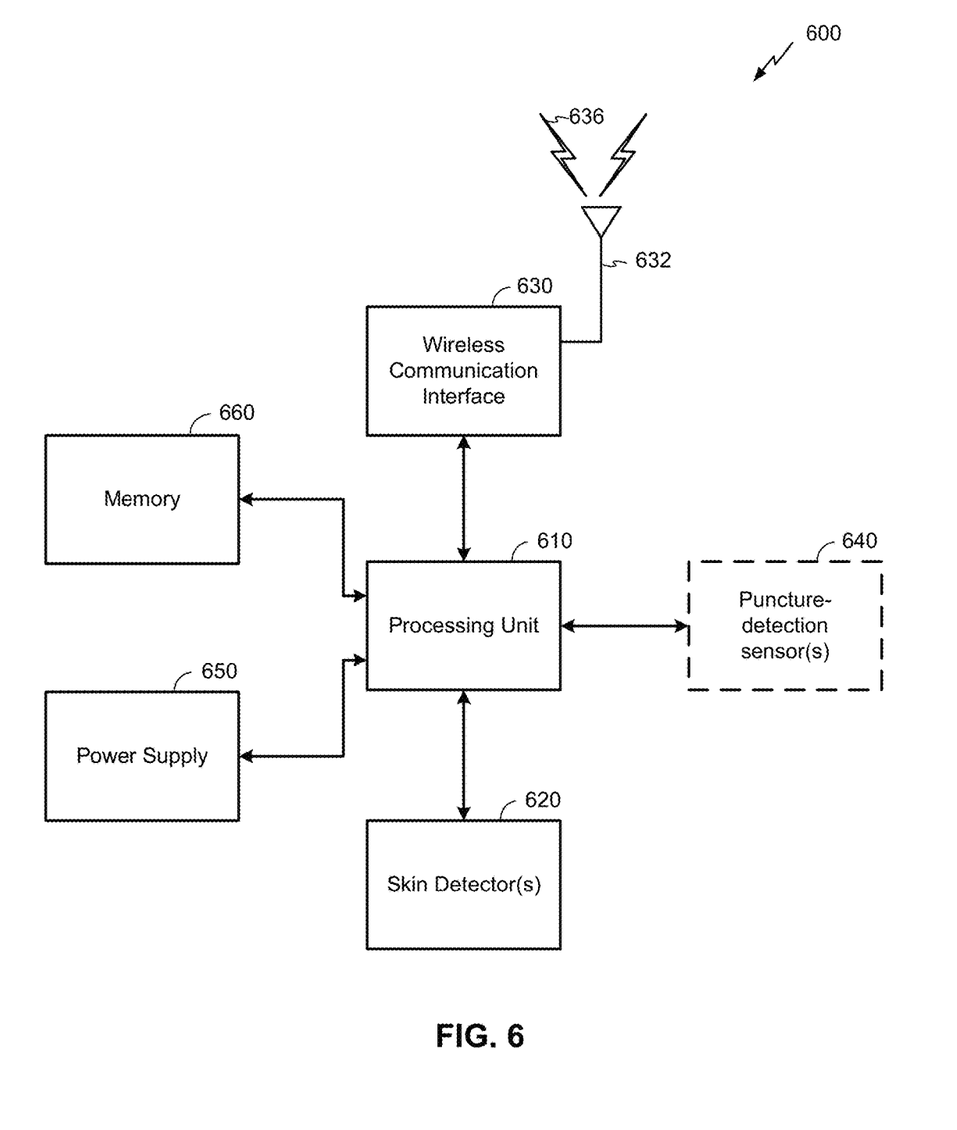
FIG. 6 is a simplified block diagram of the electrical components of a smart blister pack 110.

FIG. 6 is a simplified block diagram 600 of the electrical components of a smart blister pack 110. These components can be housed in the smart blister pack 110 (e.g., in a cavity similar to an item cavity, a separate compartment formed by top and/or bottom layers of the smart blister pack 110, etc.) and/or otherwise incorporated therein. These components comprise a processing unit 610, one or more skin detector(s) 620 (e.g., corresponding to skin detectors 240 of FIG. 2A), a power supply 650, a memory 660, a wireless communication interface 630, and an antenna 632. As noted above, embodiments may optionally include one or more puncture-detection sensor(s) 640 (e.g., corresponding to puncture-detection elements 330 of FIG. 3). Arrows between components illustrate communication and/or power links, which may be implemented by one or more buses and/or power lines. As with other figures provided herein, the embodiment illustrated here is an example. Other embodiments are not so limited, and may have additional and/or alternative features. (For example, some embodiments may include additional and/or alternative sensors to determine a triggering event to cause the smart blister pack to change from a "shelf mode" to an "active mode" as described above.)

The processing unit 610 can be used to process information provided by the skin detector(s) 620 and/or optionally puncture-detection sensor(s), as well as orchestrate the functionality of the various components illustrated in FIG. 6. The processing unit 610 may comprise without limitation one or more general-purpose processors, one or more special-purpose processors (such as digital signal processing (DSP) chips, graphics acceleration processors, application specific integrated circuits (ASICs), microprocessors, and/or the like), and/or other processing structure or means, which can be configured to perform one or more of the methods described herein. Because a smart blister pack can have a long shelf life, the processing unit may be configured to operate in an extremely low power mode that, along with the capacity of the power supply 650, can allow the electrical components of the smart blister pack to be used in after a substantially long time (e.g., a year or longer) of no use.

The skin detector(s) 620 can provide an indication of a measured capacitance, according to some embodiments. Other embodiments may utilize other techniques of measuring the presence of skin. Additionally or alternatively, skin detector(s) 620 may provide an indication of a change of capacitance. The indication may only occur if the changes are above a threshold level of capacitance.

The output of the skin detector(s) 620 can vary, depending on desired functionality. In some embodiments, the skin detector(s) 620 simply provides a measurement of capacitance to the processing unit. In other embodiments, the skin detector(s) 620 may include additional circuitry configured to provide an output only when a threshold level of change of capacitance is detected. In some embodiments, the output of the skin detector(s) 620 can enable a processing unit 610 to determine a duration of the presence (or proximity) of skin. In some embodiments each skin detector 620 may correspond to a blister of the smart blister pack such that it may be determined which blister(s) of the smart blister pack may be in contact (or proximity) of skin.

In some embodiments, the output of skin detector(s) 620 may provide for the measurement of a parameter of combined electrical characteristics. For example, capacitance (C) of a skin detector may be combined with the resistance (R) and inductance (L) of a trace (e.g., of puncture detection sensor(s) 640) to form an LCR circuit. Under the right circumstances, detection of an item extraction event can be a measurable parameter of this LCR circuit, such as the resonant frequency, the Q-point width, a related time constant, and/or the like.

As previously indicated, the operation of the skin detector(s) 620 may vary, depending on power management, manufacturing, functionality, and/or other concerns. In some embodiments, for example, the skin detector(s) 620 may be always on (e.g., periodically sampling capacitance at a given rate, without interruption). In other embodiments, triggering activities (sensor data indicating the opening of a package of the smart blister pack, an input from a puncture-detection sensor 640, etc.) may cause the skin detector(s) to begin capturing information. In other embodiments, skin detector(s) 620 may sample periodically at a low sample rate to save power, then increase the sample rate upon detection of a triggering event. As noted in the previously-described embodiments, a skin detector 620 may be situated at or near the top of each cavity such that the skin of a user's finger is in contact or near the skin detector 620 of a given cavity of the smart blister pack when extracting an item from that cavity. Some embodiments may include all or a portion of the skin detectors 620 at the bottom of a cavity (e.g., in or near the bottom layer/backing material) in cases where skin may come in contact with the backing of the smart blister pack item extraction from the cavity.

Puncture-detection sensor(s) 640 can include one or more sensors configured to provide an indication of whether bottom layer of the smart blister pack was punctured. As previously indicated, each puncture-detection sensor(s) 640 may comprise a resistive trace covering the bottom layer of a smart blister pack cavity (or other surface of the blister pack cavity likely to be pierced during removal of an item). In some embodiments, each puncture-detection sensor 640 may be associated with a particular cavity in the smart blister pack so that the processing unit 610 is provided with information regarding which cavity in the smart blister pack may have been broken. As previously indicated, the puncture-detection sensor(s) 640 may be coupled with an output (e.g., a general-purpose input/output (GPIO)) of the processing unit 610 that may cause the processing unit 610 to exit a low-power state when the puncture-detection sensor(s) 640 detects a puncture-detection event (e.g., that the bottom layer of the smart blister pack has been punctured).

As previously indicated, the processing unit 610 can use information provided by the skin detector(s) 620 and/or puncture-detection sensor(s) 640 to determine whether an item extraction event occurred, and optionally whether it may have been unintentional. To do so, the processing unit 610 may use information indicative of the presence of skin, the duration of the presence of skin, a puncture-detection event, whether the presence of skin was detected at substantially the same time (e.g., within a threshold time) that a puncture detection event occurred, whether any skin was detected when a puncture-detection event occurred, and the like. The processing unit 610 can then provide information regarding this determination to another device (e.g., the connecting device 130 of FIG. 1) via the wireless communication interface 630.

The information provided by the processing unit 610 via the wireless communication interface 630 can vary, depending on desired functionality. According to some embodiments, the information may include an indication of an item extraction event and/or whether or not the item extraction event was intentional. In some embodiments, the processing unit 610 can include a timestamp or other indication of when the item extraction event occurred. In other embodiments, the processing unit 610 can provide the sensor data itself, in which case an external device (e.g., a connecting device, remote server, etc.) may determine whether and/or when a item extraction event occurred.

In some embodiments, the processing unit 610 can be configured to provide additional information via the wireless communication interface 630. For example, the processing unit 610 may be configured to provide information regarding when a product (e.g., pills) expires, or that the product has expired. In some embodiments, the processing unit 610 can provide instructions for the item (e.g., a pill must be taken with food, once a day, etc.), which may be conveyed to a patient via a display of a connecting device, such as a mobile phone. Additionally or alternatively, the processing unit 610 may provide information regarding the identity of the product to the connecting device so that the connecting device is able to obtain instructions and/or other information (e.g., via the Internet) and provide the information to a patient.

The memory 660 may comprise, without limitation, local accessible storage (e.g., a solid-state storage component) and may include non-transitory machine-readable instructions executed by the processing unit 610. In some embodiments the processing unit 610 may fully incorporate and/or otherwise include memory 660. In some embodiments, the memory 660 may be programmable, flash-updateable, and/or the like. Such memory 660 may be configured to implement any appropriate data stores, including without limitation, various file systems, database structures, and/or the like. This memory 660 may be used to store messages and/or other information generated at or sent to/from the smart blister pack 110 and the connecting device 130, as described herein, which can be implemented using a database, linked list, or any other type of data structure. Additionally or alternatively, the messages and/or other information may be stored in a separate memory utilized by dedicated hardware for data collection.

The memory 660 also can comprise software elements (not shown), including an operating system, device drivers, executable libraries, and/or other code, such as one or more application programs, which may comprise computer programs provided by various embodiments, and/or may be designed to implement methods, and/or configure systems, provided by other embodiments, as described herein. Merely by way of example, one or more procedures described with respect to the functionality discussed above might be implemented as machine-readable code and/or instructions executable by the processing unit 610.

The power supply 650 can comprise a battery and/or other source of power for the processing unit 610 and/or other components illustrated in FIG. 6. In some embodiments, the power supply 650 can comprise a lithium-based battery (e.g., a coin cell) or other battery type configured to have a relatively long shelf life, thereby enabling the electrical components of the smart blister pack to function after long periods without use. The capacity of the power supply 650 can be determined by the power needs of the electrical components, the expected shelf life of the smart blister pack, the expected number of uses of the smart blister pack, and/or other factors.

The wireless communication interface 630 may comprise a wireless transceiver and/or a chipset (such as a Bluetooth®, Bluetooth® low energy (BLE) device, an IEEE 802.15.x (e.g., Zigbee®) device, etc.), and/or the like. The wireless communication interface 630 may permit data to be communicated with a communication device (such as the connecting device 130 of FIG. 1) and/or any other electronic devices described herein. The communication can be carried out via one or more wireless communication antenna(s) 632 that send and/or receive wireless signals 634.

Figure 7:
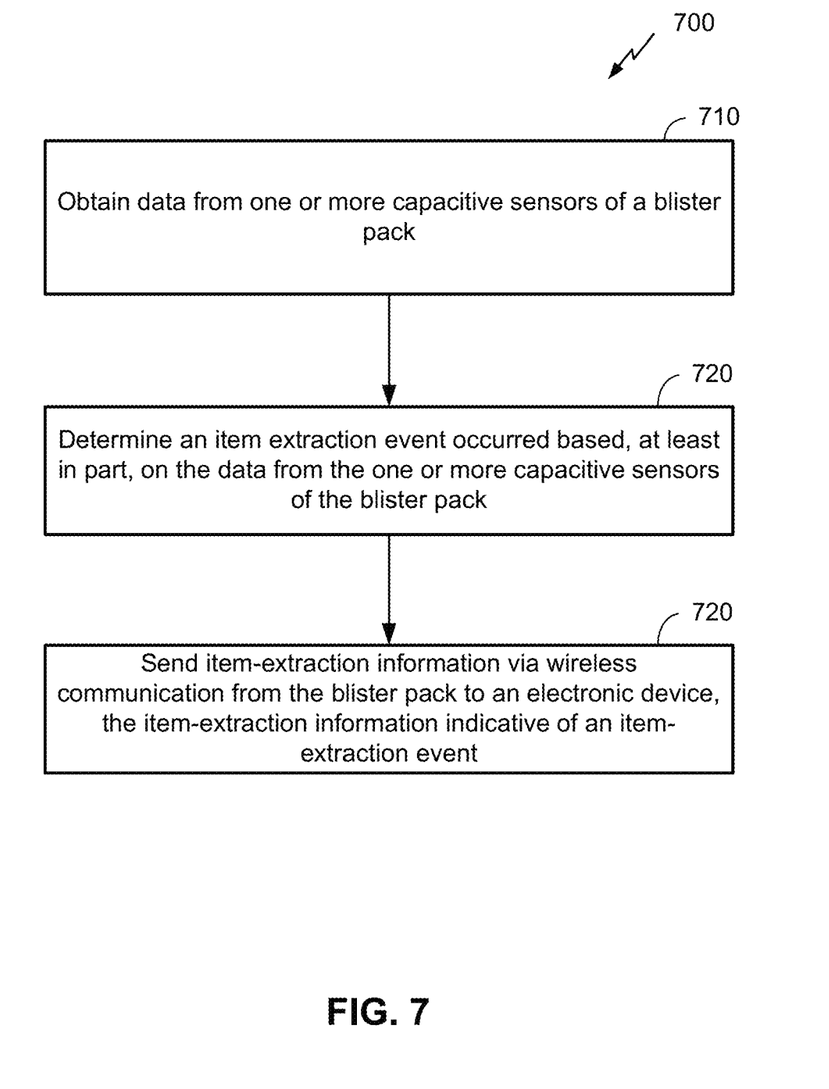
FIG. 7 is a flow diagram illustrating determining whether a pill has been extracted from a blister pack, according to one embodiment.

FIG. 7 is a flow diagram 700 illustrating determining whether an item has been extracted from a blister pack, according to one embodiment. It can be noted, however, that the embodiment provided in FIG. 7 is a non-limiting example. A person of ordinary skill in the art will recognize alternative embodiments may employ any of a variety of alterations. Any or all of the functions illustrated in the boxes of FIG. 7 can be performed by an smart blister pack (such as the smart blister pack 110 of FIG. 1 and smart blister packs described in embodiments provided herein), although alternative embodiments may enable additional or alternative devices to perform some or all of the functions.

At block 710, data from one or more capacitive sensors of the blister pack is obtained. As previously described, the one or more capacitive sensors may be configured to provide capacitance measurements (and/or another indication of the presence of skin) to a processing unit. This information may be obtained periodically by a microprocessor (e.g., by sampling capacitance with the capacitance sensor). Additionally or alternatively, a triggering event (such as a measure to change in resistivity or conductivity as indicated by one or more puncture detection sensor(s) 640) may cause a processor to exit from a low-power state and obtain information from the one or more capacitive sensors. In some embodiments, data from the one or more capacitive sensors of the blister pack may be indicative of at least a threshold increase in capacitance measured at a blister of the blister pack (e.g., showing an increase in capacitance due to the presence of a user's finger and/or deformation of the blister). In some embodiments, data from the one or more capacitive sensors of the blister pack may be indicative that the increase in capacitance measured at the blister of the blister pack has been maintained above a threshold for a time period that exceeds a time threshold (which may be an indication that the blister has been deformed). According to some embodiments, this time threshold can be set at a time long enough to indicate that the blister deformation is permanent, for example 1, 2, 5 seconds, or longer. (Of course, other embodiments may have longer or shorter time thresholds, depending on desired functionality.) Means for performing the functionality at block 710 can include, for example, the processing unit 610, skin detector(s) 620, puncture-detection sensor(s) 640, power supply 650, and/or memory 660.

At block 720, a determination is made of whether an item was extracted from the blister pack based, at least in part, on the data from the one or more capacitive sensors of the blister pack. Here, a processing unit of the blister pack and/or device remote from the blister pack can determine whether an item was extracted from the blister pack. As stated previously, this determination may be made based on the detection of skin (e.g., an increase in capacitance above a certain threshold), the duration of detection of skin (e.g., a length of time during which the capacitance is above the threshold), a puncture-detection event, a threshold difference in capacitance measured by one or more capacitive sensors at a first time and a second time, and the like. Some embodiments may further comprise obtaining puncture data indicative of a puncture of the backing material of a blister of the blister pack, where the determining of the item-extraction event occurred is further based on the puncture data, such as the voltage of a GPIO input of the processing unit changing as a result of the breakage of a puncture-detection element. In some embodiments, a processing unit of the blister pack may change from a first power state (e.g., a relatively low-power state or "shelf mode") to a second power state (e.g., a relatively high-power state or "active mode") based on the puncture data, where the processing unit of the blister pack consumes more power in the second power state than the first power state. As previously noted, determining the item-extraction event occurred may be further based on obtaining the puncture data and the data from the one or more capacitive sensors of the blister packed within a certain period of time (e.g., substantially the same time, which may indicate that a finger was used to deform the blister and push the item through the backing). The puncture data may be obtained from the physical breaking of a resistor, conductor, or other puncture-detection element located in or on the backing material. Means for performing the functionality at block 710 can include, for example, the processing unit 610, skin detector(s) 620, puncture-detection sensor(s) 640, power supply 650, and/or memory 660.

At block 730, the functionality includes sending item-extraction information via wireless communication from the blister pack to an electronic device, where the item-extraction information is indicative of an item-extraction event. As previously noted, the item-extraction information may include the indication of an item-extraction event, time-stamp indicating when the item-extraction event occurred, a likelihood that the item-extraction event was intentional, and/or the like. Means for performing the functionality at block 730 can include, for example, the processing unit 610, wireless communication interface 630, wireless communication antenna(s) 632, power supply 650, and/or memory 660.

It can be noted that, although embodiments provided herein are limited to an smart blister pack, other embodiments are not so limited. Applications of the utilization of a skin detector in the manner described herein can be found in other industries and contexts.

The methods, systems, and devices discussed herein are examples. Various embodiments may omit, substitute, or add various procedures or components as appropriate. For instance, features described with respect to certain embodiments may be combined in various other embodiments. Different aspects and elements of the embodiments may be combined in a similar manner. The various components of the figures provided herein can be embodied in hardware and/or software. Also, technology evolves and, thus, many of the elements are examples that do not limit the scope of the disclosure to those specific examples.

Reference throughout this specification to "one example", "an example", "certain examples", or "exemplary implementation" means that a particular feature, structure, or characteristic described in connection with the feature and/or example may be included in at least one feature and/or example of claimed subject matter. Thus, the appearances of the phrase "in one example", "an example", "in certain examples" or "in certain implementations" or other like phrases in various places throughout this specification are not necessarily all referring to the same feature, example, and/or limitation. Furthermore, the particular features, structures, or characteristics may be combined in one or more examples and/or features.

Some portions of the detailed description included herein are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

In the preceding detailed description, numerous specific details have been set forth to provide a thorough understanding of claimed subject matter. However, it will be understood by those skilled in the art that claimed subject matter may be practiced without these specific details. In other instances, methods and apparatuses that would be known by one of ordinary skill have not been described in detail so as not to obscure claimed subject matter.

The terms, "and", "or", and "and/or" as used herein may include a variety of meanings that also are expected to depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein may be used to describe any feature, structure, or characteristic in the singular or may be used to describe a plurality or some other combination of features, structures or characteristics. Though, it should be noted that this is merely an illustrative example and claimed subject matter is not limited to this example.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein.

Therefore, it is intended that claimed subject matter not be limited to the particular examples disclosed, but that such claimed subject matter may also include all aspects falling within the scope of appended claims, and equivalents thereof.

For an implementation involving firmware and/or software, the methodologies may be implemented with modules (e.g., procedures, functions, and so on) that perform the functions described herein. Any machine-readable medium tangibly embodying instructions may be used in implementing the methodologies described herein. For example, software codes may be stored in a memory and executed by a processor unit. Memory may be implemented within the processor unit or external to the processor unit. As used herein the term "memory" refers to any type of long term, short term, volatile, nonvolatile, or other memory and is not to be limited to any particular type of memory or number of memories, or type of media upon which memory is stored.

If implemented in firmware and/or software, the functions may be stored as one or more instructions or code on a computer-readable storage medium. Examples include computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage, semiconductor storage, or other storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

In addition to storage on computer-readable storage medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims. That is, the communication apparatus includes transmission media with signals indicative of information to perform disclosed functions. At a first time, the transmission media included in the communication apparatus may include a first portion of the information to perform the disclosed functions, while at a second time the transmission media included in the communication apparatus may include a second portion of the information to perform the disclosed functions.

What is claimed is:

1. A method of determining whether an item has been extracted from a blister pack, the method comprising:
   obtaining puncture data indicative of a puncture of backing material of one or more cavities of a plurality of cavities of the blister pack;
   obtaining data from a capacitive sensor of a plurality of capacitive sensors of the blister pack, wherein:
     each capacitive sensor of the plurality of capacitive sensors is located on a surface of a respective cavity of the plurality of cavities,
     obtaining the data from the capacitive sensor comprises sampling the capacitive sensor in response to obtaining the puncture data, and
     the data from the capacitive sensor regarding the respective cavity of the capacitive sensor, wherein the data is indicative of:
       a presence of a finger at the cavity, or
       a deformation of the cavity;
   determining, with a processing unit of the blister pack, an item-extraction event occurred based, at least in part, on:
     the data from the capacitive sensor,
     the puncture data, and
     obtaining both the puncture data and the data from the capacitive sensor within a certain period of time; and
   sending item-extraction information via wireless communication from the blister pack to an electronic device, the item-extraction information indicative of the item-extraction event.

2. The method of claim 1, wherein the data from the capacitive sensor is indicative of an increase in capacitance measured at the cavity of at least a threshold amount.

3. The method of claim 2, wherein the data from the capacitive sensor is further indicative that the increase in capacitance measured at the cavity has been maintained above the threshold for a time period that exceeds a time threshold.

4. The method of claim 1, further comprising causing the processing unit of the blister pack to change from a first power state to a second power state based on the puncture data, wherein the processing unit of the blister pack consumes more power in the second power state than in the first power state.

5. The method of claim 1, wherein the puncture data is obtained from:
    physical breaking of a resistor located in or on the backing material of the cavity, or
    physical breaking of a conductor located in or on the backing material of the cavity, or
    any combination thereof.

6. A blister pack comprising:
    a plurality of cavities;
    a plurality of capacitive sensors wherein each capacitive sensor of the plurality of capacitive sensors is located on a surface of a respective cavity of the plurality of cavities;
    puncture-detection sensors wherein each puncture-detection sensor is configured to obtain puncture data indicative of a puncture of backing material of a respective cavity;
    a processing unit communicatively coupled with the plurality of capacitive sensors and configured to:
        obtain puncture data from a puncture-detection sensor of a cavity;
        obtain data from a capacitive sensor, of the plurality of capacitive sensors, located on the surface of the cavity, wherein:
            obtaining the data from the capacitive sensor comprises sampling the capacitive sensor in response to obtaining the puncture data, and
            the data from the capacitive sensor is indicative of:
                a presence of a finger at the cavity, or
                a deformation of the cavity; and
        determine an item-extraction event occurred based, at least in part, on:
            the data from the capacitive sensor,
            the puncture data, and
            obtaining both the puncture data and the data from the capacitive sensor within a certain period of time; and
    a communication interface configured to wirelessly send item-extraction information from the blister pack to an electronic device, the item-extraction information indicative of the item-extraction event.

7. The blister pack of claim 6, wherein the capacitive sensor is configured to measure an increase in capacitance at the cavity of at least a threshold amount.

8. The blister pack of claim 7, wherein the processing unit is configured to determine that the increase in capacitance measured at the cavity has been maintained above the threshold for a time period that exceeds a time threshold.

9. The blister pack of claim 6, wherein the processing unit is further configured to change from a first power state to a second power state based on the puncture data, wherein the processing unit of the blister pack consumes more power in the second power state than in the first power state.

10. The blister pack of claim 6, wherein the puncture-detection sensors are configured to obtain the puncture data from:
    physical breaking of a resistor located in or on the backing material of the cavity, or
    physical breaking of a conductor located in or on the backing material of the cavity, or
    any combination thereof.

11. An apparatus comprising:
    means for obtaining puncture data indicative of a puncture of backing material of one or more cavities of a plurality of cavities of a blister pack;
    means for obtaining data from a capacitive sensor of a plurality of capacitive sensors of the blister pack, wherein:
        each capacitive sensor of the plurality of capacitive sensors is located on a surface of a respective cavity of the plurality of cavities,
        obtaining the data from the capacitive sensor comprises sampling the capacitive sensor in response to obtaining the puncture data, and
        the data from the capacitive sensor regarding the respective cavity of the capacitive sensor, wherein the data is indicative of:
            a presence of a finger at the cavity, or
            a deformation of the cavity;
    means for determining an item-extraction event occurred based, at least in part, on:
        the data from the capacitive sensor,
        the puncture data, and
        obtaining both the puncture data and the data from the capacitive sensor within a certain period of time; and
    means for sending item-extraction information via wireless communication from the blister pack to an electronic device, the item-extraction information indicative of the item-extraction event.

12. The apparatus of claim 11, wherein the means for obtaining data from the capacitive sensor comprises means for obtaining data indicative of an increase in capacitance measured at the cavity of at least a threshold amount.

13. The apparatus of claim 12, further comprising means for determining that the increase in capacitance measured at cavity has been maintained above the threshold for a time period that exceeds a time threshold.

14. The apparatus of claim 11, further comprising means for causing a processing means of the blister pack to change from a first power state to a second power state based on the puncture data, wherein the processing means of the blister pack consumes more power in the second power state than in the first power state.

15. The apparatus of claim 11, wherein the means for obtaining puncture data comprise means for obtaining puncture data from:
    physical breaking of a resistor located in or on the backing material of the cavity, or
    physical breaking of a conductor located in or on the backing material of the cavity, or
    any combination thereof.

16. A non-transitory computer-readable medium having instructions embedded thereon for determining whether an item has been extracted from a blister pack, the instructions including computer code for:
    obtaining puncture data indicative of a puncture of backing material of one or more cavities of a plurality of cavities of the blister pack;
    obtaining data from a capacitive sensor of a plurality of capacitive sensors of the blister pack, wherein:
        each capacitive sensor of the plurality of capacitive sensors is located on a surface of a respective cavity of the plurality of cavities,
        obtaining the data from the capacitive sensor comprises sampling the capacitive sensor in response to obtaining the puncture data, and
        the data from the capacitive sensor regarding the respective cavity of the capacitive sensor, wherein the data is indicative of:

a presence of a finger at the cavity, or a deformation of the cavity;

determining an item-extraction event occurred based, at least in part, on:

the data from the capacitive sensor, the puncture data, and obtaining both the puncture data and the data from the capacitive sensor within a certain period of time; and sending item-extraction information via wireless communication from the blister pack to an electronic device, the item-extraction information indicative of the item-extraction event.

17. The non-transitory computer-readable medium of claim 16, wherein the computer code for obtaining data from the capacitive sensor comprises computer code for obtaining data indicative of an increase in capacitance measured at the cavity of at least a threshold amount.

18. The non-transitory computer-readable medium of claim 17, further comprising computer code for determining that the increase in capacitance measured at the cavity has been maintained above the threshold for a time period that exceeds a time threshold.

19. The non-transitory computer-readable medium of claim 16, further comprising computer code for causing a processing unit of the blister pack to change from a first power state to a second power state based on the puncture data, wherein the processing unit of the blister pack consumes more power in the second power state than in the first power state.

20. The non-transitory computer-readable medium of claim 16, wherein the computer code for obtaining puncture data comprise means for obtaining puncture data from:

physical breaking of a resistor located in or on the backing material of the blister of the cavity, or physical breaking of a conductor located in or on the backing material of the blister of the cavity, or any combination thereof.

* * * * *